United States Patent
Duggineni et al.

(10) Patent No.: US 8,137,361 B2
(45) Date of Patent: Mar. 20, 2012

(54) METHOD AND APPARATUS FOR CONSTANT FORCE TENSOR/LIGAMENT BALANCER

(75) Inventors: Rajesh V. Duggineni, Warsaw, IN (US); Radu Serban, Warsaw, IN (US); Daniel Norton, Indianapolis, IN (US); David Wycliffe Murray, Oxford (GB)

(73) Assignee: Biomet Manufacturing Corp., Warsaw, IN (US)

( * ) Notice: Subject to any disclaimer, the term of this patent is extended or adjusted under 35 U.S.C. 154(b) by 653 days.

(21) Appl. No.: 12/252,819

(22) Filed: Oct. 16, 2008

(65) Prior Publication Data

US 2010/0100102 A1  Apr. 22, 2010

(51) Int. Cl.
 A61B 17/58 (2006.01)
 A61B 17/60 (2006.01)
 A61F 2/00 (2006.01)
(52) U.S. Cl. .................. 606/102; 606/86 R; 606/90
(58) Field of Classification Search .................. 606/102, 606/124, 86 R, 86 A, 99
See application file for complete search history.

(56) References Cited

U.S. PATENT DOCUMENTS

| | | | |
|---|---|---|---|
| 4,501,266 A | 2/1985 | McDaniel | |
| 5,213,112 A | 5/1993 | Niwa et al. | |
| 5,468,244 A | 11/1995 | Attfield et al. | |
| 5,540,696 A | 7/1996 | Booth, Jr. et al. | |
| 5,630,820 A | 5/1997 | Todd | |
| 5,799,432 A * | 9/1998 | Wright et al. | 42/1.02 |
| 5,800,438 A * | 9/1998 | Tuke et al. | 606/90 |
| 6,003,584 A * | 12/1999 | Weinreich | 160/191 |
| 6,022,377 A | 2/2000 | Nuelle et al. | |
| 6,648,896 B2 | 11/2003 | Overes et al. | |
| 6,758,850 B2 | 7/2004 | Smith et al. | |
| 7,156,853 B2 | 1/2007 | Muratsu et al. | |
| 7,172,561 B2 | 2/2007 | Grinberg | |
| 2003/0075026 A1* | 4/2003 | Schulz et al. | 81/413 |
| 2004/0225320 A1* | 11/2004 | Kulcinski et al. | 606/198 |
| 2005/0125010 A1* | 6/2005 | Smith et al. | 606/142 |

* cited by examiner

*Primary Examiner* — Thomas C. Barrett
*Assistant Examiner* — Samuel Hanna
(74) *Attorney, Agent, or Firm* — Harness, Dickey (57) ABSTRACT

A tensor/ligament balancer for use in measuring a gap existing between an anatomy is provided. The tensor/ligament balancer can include a first paddle. The tensor/ligament balancer can also include a second paddle movable relative to the first paddle. The tensor/ligament balancer can further include a biasing member operable to apply a substantially constant force on the second paddle to move the second paddle relative to the first paddle. At a first position, the second paddle can be substantially adjacent to the first paddle. The second paddle can be automatically movable away from the first paddle to a second position by applying the substantially constant force to the second paddle.

7 Claims, 4 Drawing Sheets

METHOD AND APPARATUS FOR CONSTANT FORCE TENSOR/LIGAMENT BALANCER

FIELD

The present disclosure relates generally to surgical instruments and procedures, and more specifically, to a method and apparatus for a constant force tensor/ligament balancer.

BACKGROUND

The statements in this section merely provide background information related to the present disclosure and may not constitute prior art.

Many portions of the human anatomy naturally articulate relative to one another. Generally, the articulation between the portions of the anatomy is substantially smooth and without abrasion. This articulation is allowed by the presence of natural tissues, such as cartilage and strong bone.

Over time, however, due to injury, stress, degenerative health issues and various other issues, articulation of the various portions of the anatomy can become rough or impractical. For example, injury can cause the cartilage or the boney structure to become weak, damaged, or non-existent. Therefore, the articulation of the anatomical portions is no longer possible for the individual.

At such times, it can be desirable to replace the anatomical portions with a prosthetic portion such that normal or easy articulation can be reproduced. For example, a distal end of a femur naturally articulates with respect to a tibia to form a knee joint. After injury or other degenerative processes, the distal end of the femur and the tibia and can become rough or damaged. In these cases, it may be desirable to replace at least a portion of the tibia and/or femur with a prosthesis.

In order to replace the tibia and/or femur with a prosthesis, such as a tibial prosthesis and/or a femoral prosthesis, one or more cuts may be made to resect the distal ends of the tibia and/or femur. Prior to coupling the tibial prosthesis and/or femoral prosthesis to the respective resected bone(s), a gap existing between the resected tibia and the resected femur in flexion and extension may be measured. The gap in flexion ("flexion gap") and the gap in extension ("extension gap") may generally be about equal to ensure knee stability and full range of motion after the tibial prosthesis and/or femoral prosthesis are coupled to the respective resected bone(s).

The gap in flexion and the gap in extension may be measured using a tensor/ligament balancer. Currently, the surgeon may measure the gap in flexion and the gap in tension under a varying output force. Thus, a surgeon using the tensor/ligament balancer may have to pay close attention to the amount of force used to measure the gap in tension and the amount of force used to measure the gap in extension to ensure an accurate measurement.

SUMMARY

A tensor/ligament balancer for use in measuring a gap existing between an anatomy is provided. The tensor/ligament balancer can include a first paddle. The tensor/ligament balancer can also include a second paddle movable relative to the first paddle. The tensor/ligament balancer can further include a biasing member operable to apply a substantially constant force on the second paddle to move the second paddle relative to the first paddle. At a first position, the second paddle can be substantially adjacent to the first paddle. The second paddle can be automatically movable away from the first paddle to a second position by applying the substantially constant force to the second paddle.

A tensor/ligament balancer for use in measuring a gap existing between an anatomy is provided. The tensor/ligament balancer can include a body, and at least one first paddle coupled to the body. The tensor/ligament balancer can also include a trigger pivotably coupled to the body and operable to move towards the body in a first, actuated position and away from the body in a second, released position. The tensor/ligament balancer can include at least one second paddle moveable by the trigger. The tensor/ligament balancer can include a measurement tensor system coupled to the at least one second paddle and the trigger. At least a portion of the measurement system can be moveable relative to the body. The measurement system can include at least one biasing member operable by the trigger to apply a constant force on the at least one second paddle to enable the at least one second paddle to move relative to the body to measure the gap.

Further provided is a tensor/ligament balancer for use in measuring a gap existing between an anatomy. The tensor/ligament balancer can comprise a body having a handle and defining a slot. The tensor/ligament balancer can include at least one first paddle coupled to the body, and a trigger pivotably coupled to the body. The trigger can be operable to pivot towards the handle in a first, actuated position and away from the handle in a second, released position. The tensor/ligament balancer can include a spring housing coupled to the trigger and constrained to move in one direction relative to the body based on the movement of the trigger between the first, actuated position and the second, released position. The spring housing can be received within the slot of the body and can include at least one measurement indicia such that the movement of the spring housing relative to the slot enables measurement of the gap. The tensor/ligament balancer can include a clock spring disposed in the spring housing and coupled to the trigger. The clock spring can be operable to be wound by the trigger when the trigger is pivoted into the first, actuated position, and can be operable to unwind when the trigger pivots into the second, released position. The tensor/ligament balancer can include at least one second paddle coupled to the spring housing such that the at least one second paddle moves with the spring housing. The movement of the trigger from the first, actuated position to the second, released position can move the at least one second paddle relative to the body to align the at least one measurement indicia of the spring housing with the slot in the body to enable measurement of the gap.

Also provided is a method of measuring a gap existing between an anatomy. The method can include positioning a joint in flexion or extension. The method can include compressing at least two paddles substantially adjacent to one another. The method can include positioning the least two paddles within the joint, and releasing the at least two paddles to automatically separate the at least two paddles to measure a gap between the joint in flexion or extension.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. Although the following description is related generally to a constant force tensor/ligament balancer that can be used to measure a gap between a resected tibia and/or resected femur, it will be understood that the constant force tensor/ligament balancer, as described and claimed herein, can be used with any appropriate surgical procedure. In addition, although a tensor/ligament balancer is illustrated and described herein as being used with a unicompartmental knee replacement procedure, it will be understood that the tensor/ligament balancer can be used in a total knee replacement procedure. Therefore, it will be understood that the following discussions are not intended to limit the scope of the appended claims.

Figure 1:
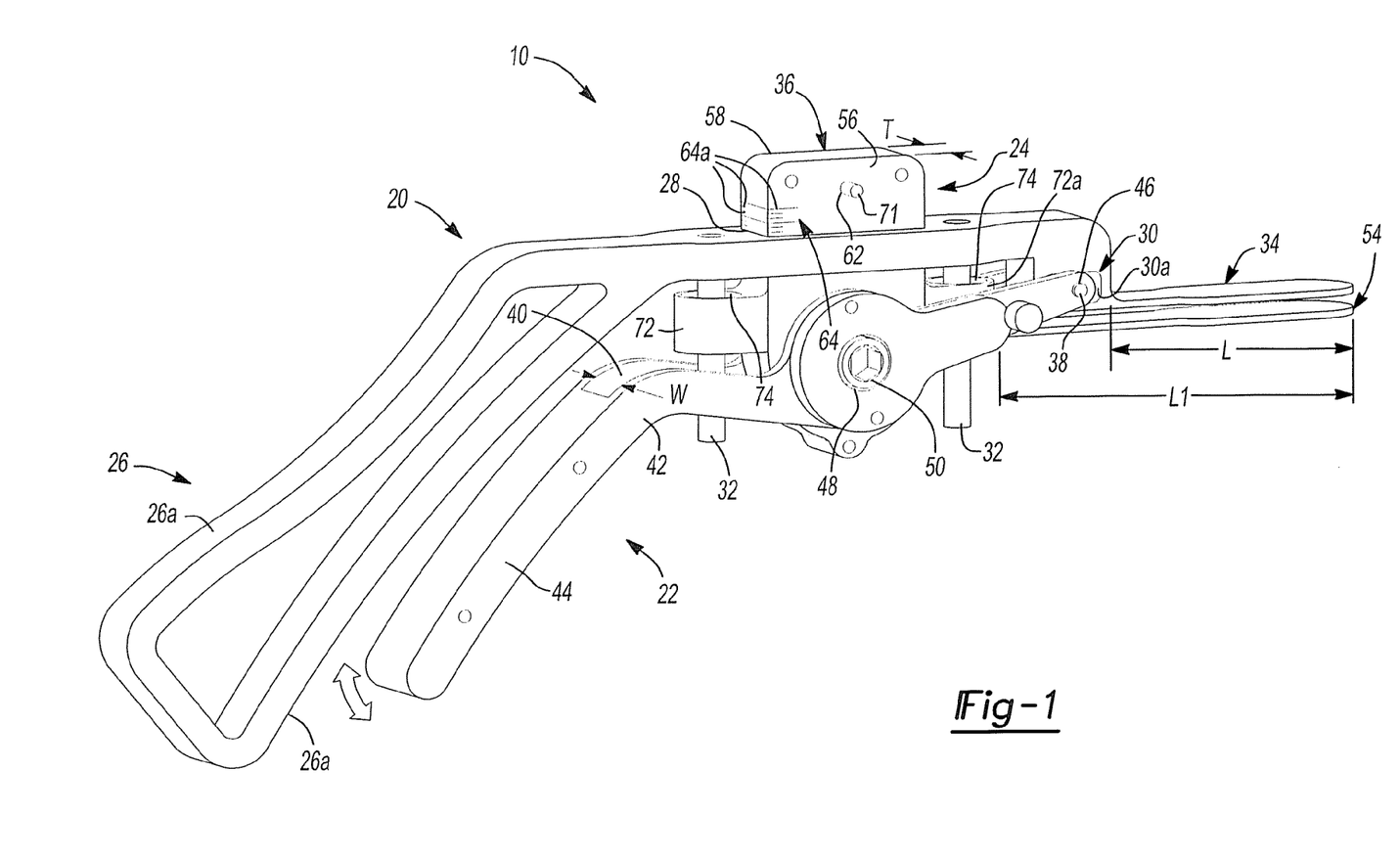
FIG. 1 is a perspective view of a method and apparatus for a constant force tensor/ligament balancer according to the present disclosure.
Figure 2:
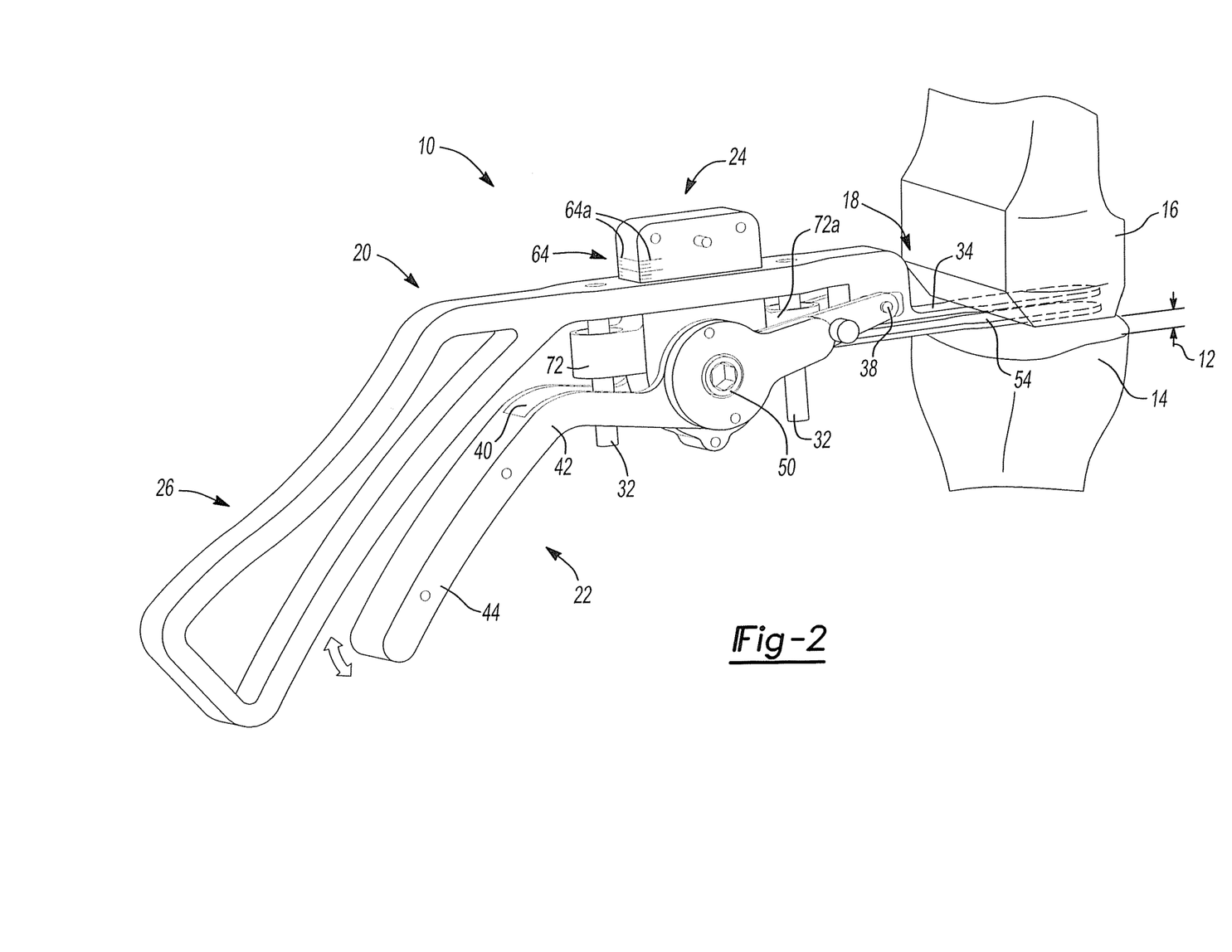
FIG. 2 is an environmental view of the system of FIG. 1 in an anatomy positioned in extension.
Figure 4:
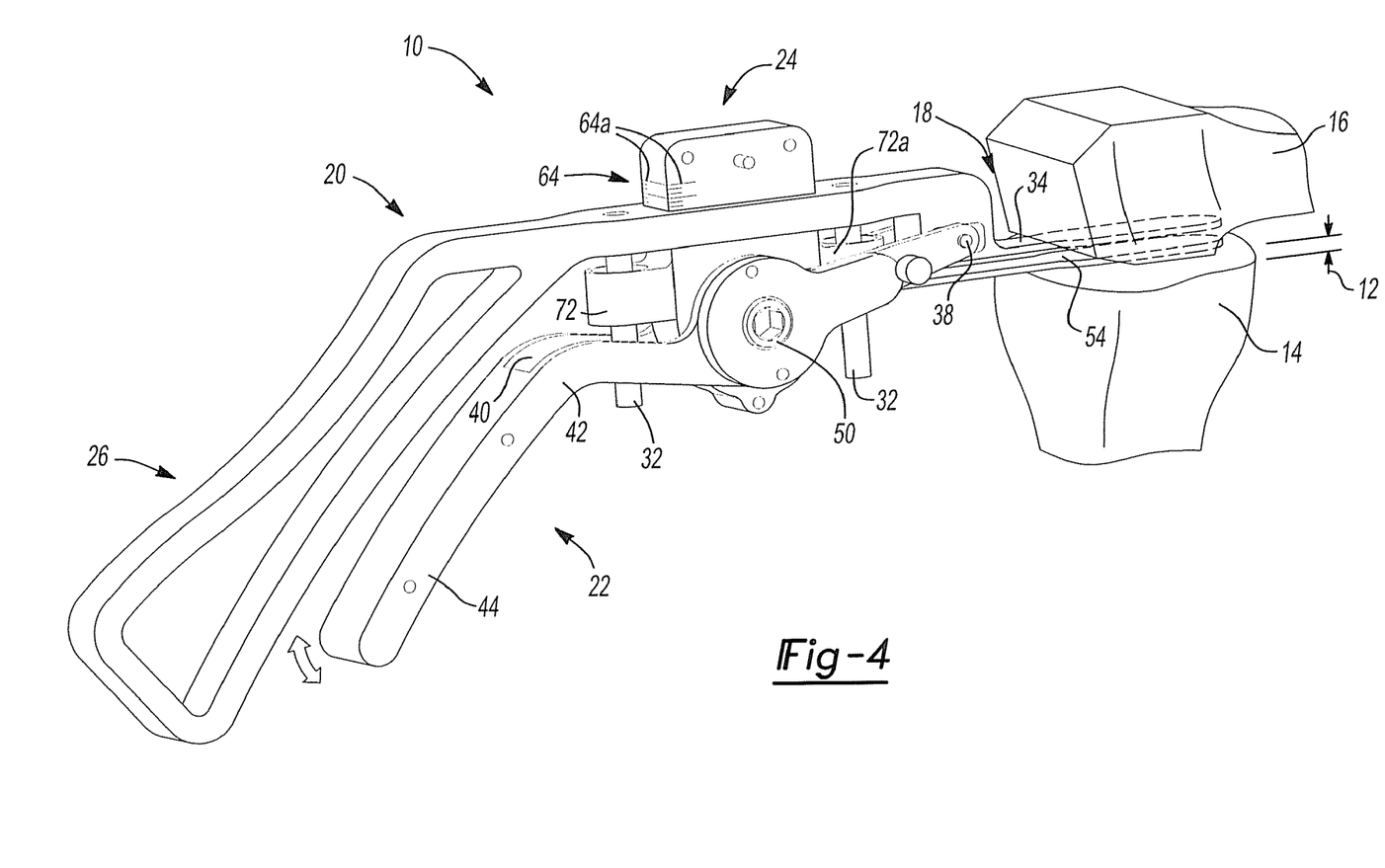
FIG. 4 is an environmental view of the system of FIG. 1 in an anatomy positioned in flexion.

With reference to FIGS. 1 and 2, a constant force tensor/ligament balancer 10 is shown. The tensor/ligament balancer 10 can be used to measure a gap 12 existing between two surfaces, such as a resected tibial surface 14 and a resected femoral surface 16 in either a unicompartmental knee replacement or a total knee replacement procedure. For example, as shown in FIG. 2, in a unicompartmental knee replacement procedure the tensor/ligament balancer 10 can be inserted between the resected tibial surface 14 and the resected femoral surface 16 when a knee joint 18 is extended to measure a length of the gap 12 ("extension gap"). In addition, the tensor/ligament balancer 10 can be used to measure the gap 12 when the resected tibial surface 14 and the resected femoral surface 16 are placed in flexion ("flexion gap") as shown in FIG. 4. With reference to FIGS. 1 and 2, the tensor/ligament balancer 10 can include a body 20, a trigger 22 and a measurement tension system 24.

The body 20 can include a graspable portion or handle 26, which defines a slot 28, a pivot axis 30, at least one post 32 and a first paddle 34. The body 20 can comprise a one-piece monolithic structure, and thus, the handle 26, the slot 28, the pivot axis 30 and the first paddle 34 can be integrally formed in the body 20. The body 20 can be composed of any suitable biocompatible material, such as a biocompatible metal, metal alloy or polymer.

The handle 26 can comprise any structure graspable by a surgeon, and thus, will not be discussed in great detail herein. Briefly, however, the handle 26 can include concave members 26a. It should be understood, that although the handle 26 is illustrated and described herein as having the concave members 26a, the handle 26 can have any suitable shape. One of the concave members 26a can be sized to mate with a palm of the surgeon, and thus, can improve the ergonomics of the handle 26. A second one of the concave members 26a can be shaped to mate with the trigger 22 when the trigger 22 is depressed or retracted by the surgeon, as will be discussed herein.

The slot 28 can enable the measurement tension system 24 to move relative to the body 20. Generally, the slot 28 can be configured to slideably receive a spring housing 36 associated with the measurement tension system 24. Typically, the slot 28 can be rectangular, however, any suitable shape could be employed, depending upon the shape of the spring housing 36, such as annular, oblong, oval, square, etc. The position of the spring housing 36 relative to the slot 28 can enable a surgeon to measure the gap 12 between the resected tibial surface 14 and the resected femoral surface 16 (FIG. 2), and thus, the slot 28 can act as a sight line for the surgeon, as will be discussed. The pivot axis 30 can enable the trigger 22 to pivot relative to the body 20. The pivot axis 30 can generally include a bore 30a for receipt of a pivot pin 38. The pivot pin 38 can pivotally couple the trigger 22 to the body 20.

The at least one post 32 can comprise two posts 32. The measurement tension system 24 and the trigger 22 can be slideably coupled to the posts 32. The posts 32 can be configured to direct or guide the movement of the measurement tension system 24 relative to the body 20. In this regard, the posts 32 can allow for parallel movement of the measurement tension system 24, as will be discussed herein. Thus, the posts 32 can also serve to define a range of motion for the measurement tension system 24 relative to the body 20. The posts 32 can also direct or guide the movement of the trigger 22 relative to the body 20.

The first paddle 34 can be integrally formed with the body 20, and can extend from the pivot axis 30. The first paddle 34 can have a length L that can be sized to enable the surgeon to place the first paddle 34 adjacent to an anatomy, such as the resected femoral surface 16 (FIG. 2). Generally, the first paddle 34 can provide a baseline for the measurement of the gap 12 between the resected tibial surface 14 and the resected femoral surface 16, as will be discussed herein.

The trigger 22 can be pivotally coupled to the body 20, via the pivot pin 38 of the pivot axis 30. The trigger 22 can be depressed or actuated prior to the insertion of the tensor/ligament balancer 10 into an anatomy, such as a knee joint 18, and can be released to measure the gap 12 between the resected tibial surface 14 and the resected femoral surface 16. The trigger 22 can include a first member 40, a second member 42 and an actuator 44. The first member 40 and second member 42 can extend from the actuator 44. The first member 40 and the second member 42 can be separated by a width W, which can be substantially about equal to a thickness T of the spring housing 36 to enable the spring housing 36 to be received between the first member 40 and second member 42 of the trigger 22. The first member 40 and the second member 42 can be symmetrical about a center axis of the actuator 44, and each of the first member 40 and the second member 42 can define a pivot bore 46 and a bore 48.

The pivot bore 46 can receive a portion of the pivot pin 38 to enable the trigger 22 to pivot relative to the body 20. The bore 48 can couple the trigger 22 to the measurement tension system 24. In this regard, the bore 48 can receive a shaft 50 of the measurement tension system 24 to couple the measurement tension system 24 to the trigger 22. For example, the bore 48 can include threads that can mate with threads formed on the shaft 50, or the shaft 50 can pass through the bore 48 and be threaded into a nut. Generally, however, the shaft 50 can be coupled to the trigger 22, via any suitable mechanical fastening technique, such that the shaft 50 moves with the trigger 22 as the trigger 22 pivots. As the measurement tension system 24 is coupled to the trigger 22, the measurement tension system 24 can move with the trigger 22, as will be discussed herein.

The actuator 44 of the trigger 22 can comprise any suitable graspable member that the surgeon can retract or depress to pivot the trigger 22 relative to the body 22. Generally, the actuator 44 can comprise an elongated member that can be shaped to mate with one of the concave members 26a of the handle 26, however, it will be understood that the actuator 44 could have any desired shape. When the actuator 44 is retracted or depressed by the surgeon, the trigger 22 can be pivoted relative to the body 20, which in turn can move the measurement tension system 24 relative to the body 20.

Figure 3:
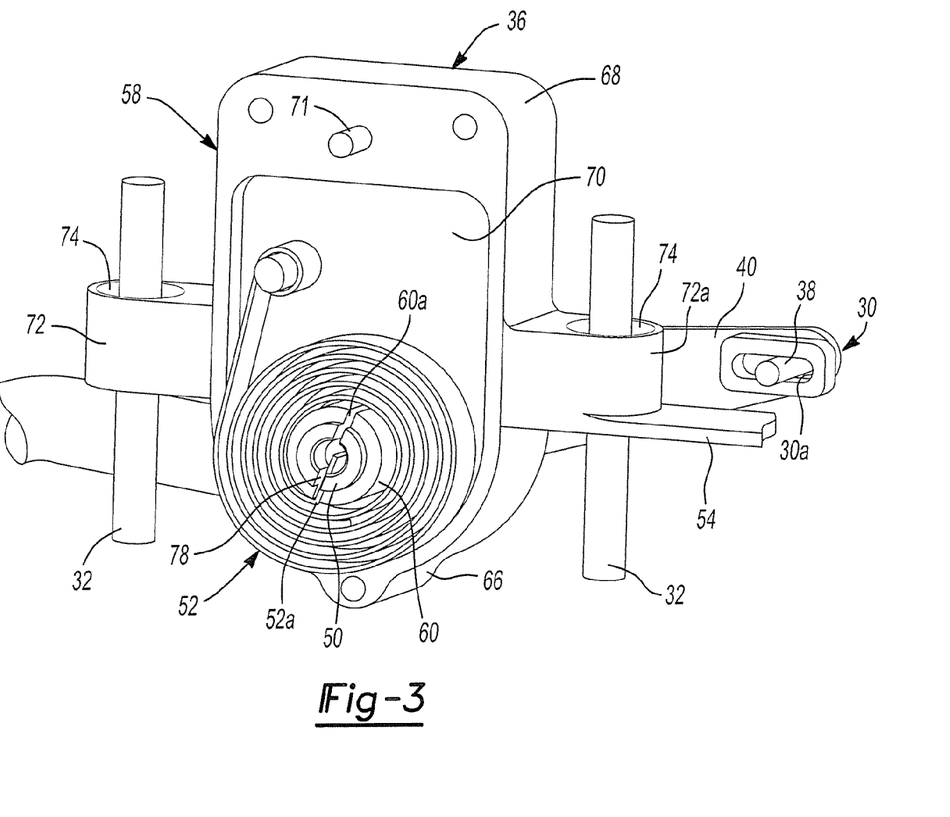
FIG. 3 is a schematic environmental view of the system of FIG. 1 in an anatomy.

With reference to FIGS. 1-3, the measurement tension system 24 can include the spring housing 36, the shaft 50, a tensioner or spring 52 (FIG. 3) and a second paddle 54. The spring housing 36 can encase the spring 52, and can include a first or cover portion 56, a second or body portion 58 and a throughbore 60 (FIG. 3). The cover portion 56 can enclose the body portion 58, and can include at least one aperture 62 and a measurement scale 64. The at least one aperture 62 can receive a post 71 of the body portion 58 to couple the cover portion 56 to the body portion 58. It will be understood, however, that the cover portion 56 can be coupled to the body portion 58 through any suitable technique, such as press-fit, snap-fit, rivets, interlocking protrusions, etc.

The measurement scale 64 can provide multiple measurement indicia 64a to enable the surgeon to measure the gap 12 existing between the resected tibial surface 14 and the resected femoral surface 16 (FIGS. 2 and 4). Typically, the measurement scale 64 can be in millimeters, and the measurement indicia 64a can range from about 1 millimeter to about 15 millimeters. The measurement scale 64 can be formed on the cover portion 56 through any suitable technique, such as stamping, etching, engraving, etc. Generally, the measurement scale 64 can be formed on the cover portion 56 such that when the cover portion 56 is adjacent to the slot 28 formed in the body 20, the surgeon can easily read the measurement indicia 64a.

With reference to FIG. 3, the body portion 58 can define a first end 66, a second end 68, a cavity 70 that extends between the first end 66 and the second end 68, the post 71 and two guides 72. The body portion 58 can also include the measurement scale 64 and measurement indicia 64a formed on the cover portion 56, if desired, to enable the surgeon to view the measurement from a plurality of different viewpoints (FIG. 1). The first end 66 can be generally arcuate in shape for receipt of the spring 52, and the second end 68 can be generally rectangular in shape to enable the second end 68 to pass through the slot 28 of the body 20. The cavity 70 can be configured to receive the spring 52 therein. The post 71 can be extend from the body portion 58 to assist in coupling the cover portion 56 to the body portion 58.

The two guides 72 can be coupled to the body portion 58 between the first end 66 and the second end 68. The guides 72 can each define a bore 74 for receipt of the posts 32. Generally, the bores 74 can be sized to enable the spring housing 36 to translate or slide with respect to the posts 32. The guides 72 can cooperate with the posts 32 to constrain the spring housing 36 such that the spring housing 36 moves generally in one direction. Typically, the spring housing 36 can move in a direction perpendicular to the first paddle 34 and the second paddle 54. The posts 32 and guides 72 can also cooperate to enable the first paddle 34 and the second paddle 54 to move in a direction parallel to each other. The second paddle 54 can extend from a first one of the guides 72a such that the lower paddle 54 can move with the spring housing 36, as will be discussed herein.

The throughbore 60 can receive the shaft 50 to couple the spring housing 36 to the trigger 22, and can include a slot 60a for receipt of a portion of the spring 52. In this regard, the shaft 50 can be fixedly coupled to the spring housing 36 via the throughbore 60 so that the movement of the trigger 22 from a depressed or actuated position into a released or unactuated position can cause the shaft 50, and thus, the spring housing 36, to move with respect to the body 20. The shaft 50 can define a slot 78 for receipt of a portion of the spring 52. The slot 78 can enable the spring 52 to be coupled to the shaft 50, such that the movement of the shaft 50 can compress the spring 52, as will be discussed. In addition, a washer can be received onto the shaft 50 to assist in retaining the spring 52 on the shaft 50, if desired. **\*\*INVENTOR: Please verify.\*\***

With reference to FIG. 3, the spring 52 can be received and retained within the cavity 70 of the spring housing 36. The spring 52 can comprise a clock spring, which can include a bent end 52a. The bend end 52a can couple the spring 52 to the shaft 50. It should be understood that although the spring 52 is described and illustrated herein as comprising a clock spring, any suitable biasing member could be employed, such as a coil spring. As the spring 52 is coupled to the shaft 50, which is coupled to the trigger 22, the depression or actuation of the trigger 22 can compress or wind the spring 52 while moving the spring housing 36 in a first or upward direction. When the trigger 22 is released, the spring 52 can unwind, which can substantially automatically move the shaft 50, and thus, the spring housing 36 in a second or downward direction until the second paddle 54 contacts an anatomy, such as the resected tibial surface 14, as will be discussed. The spring 52 when the trigger 22 is released, can exert a generally constant force on the second paddle 54, and thus, can ensure that a constant force is used to measure the gap 12 in flexion (FIG. 4) and in extension (FIG. 2).

With reference to FIG. 1, the second paddle 54 can extend from the guide 72a. The second paddle 54 can have a length L1 that enable the surgeon to place the first paddle 34 and the second paddle 54 adjacent to an anatomy (as illustrated in FIGS. 2 and 4) when the trigger 22 is depressed or actuated. When the surgeon releases the trigger 22, the second paddle 54 can move in a direction parallel to the first paddle 34 due to the unwinding of the spring 52 until the second paddle 54 contacts the resected tibial surface 14, as will be discussed (FIGS. 2 and 4). Thus, the second paddle 54 can serve to measure the gap 12 with a constant force applied by the spring 52.

In order to employ the tensor/ligament balancer 10 to measure a gap 12 in the anatomy, such as the knee joint 18, with reference to FIGS. 2 and 4, the tensor/ligament balancer 10 can be inserted into the knee joint 18. For example, with reference to FIG. 2, the knee joint 18 can be placed in extension. Then, generally, the surgeon can depress or actuate the trigger 22 so that the second paddle 54 is adjacent to the first paddle 34 prior to the insertion of the tensor/ligament balancer 10 into the anatomy. As the surgeon depresses the trigger 22, the shaft 50 can wind the spring 52 and move the spring housing 36 in the first or upward direction, thereby moving the second paddle 54 in the first or upward direction until the second paddle 54 is adjacent to the first paddle 34. With the first paddle 34 adjacent to the second paddle 54, the surgeon can insert the tensor/ligament balancer 10 adjacent to the resected femoral surface 16. Then, the surgeon can release the trigger 22.

By releasing the trigger 22, the spring 52 can unwind. The unwinding of the spring 52 can substantially automatically move the shaft 50 in the second or downward direction, which can move the spring housing 36 and second paddle 54 in the second or downward direction until the second paddle 54 is adjacent to the resected tibial surface 14. Once the second paddle 54 is adjacent to or in contact with the resected tibial surface 14, the surgeon can read the measurement indicia 64a to determine the length of the gap 12. The surgeon can then depress or actuate the trigger 22 to move the second paddle 54 adjacent to the first paddle 34 so that the tensor/ligament balancer 10 can be removed from the knee joint 18.

This procedure can be repeated to measure the gap 12 in both flexion and extension. In this regard, the surgeon can position the knee join 18 into flexion, as shown in FIG. 4. Then, the surgeon can depress or actuate the trigger 22 so that the second paddle 54 is adjacent to the first paddle 34 prior to the insertion of the tensor/ligament balancer 10 into the anatomy. As the surgeon depresses the trigger 22, the shaft 50 can wind the spring 52 and move the spring housing 36 in the first or upward direction, thereby moving the second paddle 54 in the first or upward direction until the second paddle 54 is adjacent to the first paddle 34. With the first paddle 34 adjacent to the second paddle 54, the surgeon can insert the tensor/ligament balancer 10 adjacent to the resected femoral surface 16. Then, the surgeon can release the trigger 22.

By releasing the trigger 22, the spring 52 can unwind. The unwinding of the spring 52 can substantially automatically move the shaft 50 in a second or downward direction, which can move the spring housing 36 and second paddle 54 in the second or downward direction until the second paddle 54 is adjacent to the resected tibial surface 14. Once the second paddle 54 is adjacent to or in contact with the resected tibial surface 14, the surgeon can read the measurement indicia 64a to determine the length of the gap 12. The release of the trigger 22 can apply substantially the same output force to the second paddle 54 each time, which can ensure consistency in the measurement. The surgeon can then depress or actuate the trigger 22 to move the second paddle 54 adjacent to the first paddle 34 so that the tensor/ligament balancer 10 can be removed from the knee joint 18.

As the spring 52 provides a constant output force to the second paddle 54 during the measurement procedure, the surgeon does not need to measure the output force of the tensor/ligament balancer 10 when used to measure the gap in flexion and the gap in tension to ensure that the output force is the same. This can reduce the complexity of the measurement procedure, while also improving the accuracy of the measurement values observed by the surgeon. In addition, the use of the spring 52 can serve to balance the force of the ligments acting on the knee joint, which can further ensure that the force on the knee joint 18 is the same in flexion and extension.

It should be noted that although the tensor/ligament balancer 10 is described herein for use in a uni-compartmental knee, it will be understood that the tensor/ligament balancer 10 can be used in a total knee replacement procedure. In this regard, the tensor/ligament balancer 10 can include two first paddles 34a, 34b and two second paddles 54a, 54b. Each of the first paddles 34a, 34b and each of the second paddles 54a, 54b can be separated by a distance D, which can be about equivalent to a medial-lateral distance between each condyle 16a, 16b of the resected femoral surface 16. In addition, each of the first paddles 34a, 34b and each of the second paddles 54a, 54b can be independently tensioned by springs 52a, 52b, and thus, can include two measurement tension systems 24a, 24b, which can be employed to measure the gap 12a, 12b of a total knee joint in both extension and flexion.

While specific examples have been described in the specification and illustrated in the drawings, it will be understood by those of ordinary skill in the art that various changes can be made and equivalents can be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. A tensor/ligament balancer for use in measuring a gap existing between an anatomy, comprising:
    a body having a handle and defining a slot;
    at least one first paddle coupled to the body;
    a trigger pivotably coupled to the body and operable to pivot towards the handle in a first, actuated position and away from the handle in a second, released position;
    a spring housing coupled to the trigger and constrained to move in one direction relative to the body based on the movement of the trigger between the first, actuated position and the second, released position, the spring housing received within the slot of the body and including at least one measurement indicia such that the movement of the spring housing relative to the slot enables measurement of the gap;
    a clock spring disposed in the spring housing and coupled to the trigger, the clock spring operable to be wound by the trigger when the trigger is pivoted into the first, actuated position, and operable to unwind when the trigger pivots into the second, released position;
    at least one second paddle coupled to the spring housing such that the at least one second paddle moves with the spring housing and such that the clock spring biases the at least one second paddle away from the at least one first paddle; and
    wherein the movement of the trigger from the first, actuated position to the second, released position moves the at least one second paddle relative to the body to align the at least one measurement indicia of the spring housing with the slot in the body to enable measurement of the gap.

2. The tensor/ligament balancer of claim 1, wherein the trigger further comprises:

a first member;

a second member spaced apart from the first member; and wherein the spring housing is coupled between the first member and the second member.

3. The tensor/ligament balancer of claim 2, wherein a shaft couples the spring housing to the first member and the second member, the shaft including a slot for receipt of a portion of the clock spring such that the movement of the trigger into the first, actuated position winds the clock spring.

4. The tensor/ligament balancer of claim 3, wherein body includes at least one post, and the spring housing includes at least one guide for receipt of the at least one post to enable the spring housing to move relative to the body in one direction.

5. The tensor/ligament balancer of claim 4, wherein the at least one second paddle is coupled to the at least one guide.

6. The tensor/ligament balancer of claim 5, wherein the at least one first paddle and the at least one second paddle are configured to measure a gap between a prepared portion of a knee joint.

7. The tensor/ligament balancer of claim 6, wherein the clock spring provides a constant output force to move the at least one second paddle apart from the at least one first paddle within the anatomy to enable the measurement of the gap.

* * * * *

UNITED STATES PATENT AND TRADEMARK OFFICE
CERTIFICATE OF CORRECTION

| | | |
|---|---|---|
| PATENT NO. | : 8,137,361 B2 | Page 1 of 1 |
| APPLICATION NO. | : 12/252819 | |
| DATED | : March 20, 2012 | |
| INVENTOR(S) | : Rajesh Duggineni et al. | |

It is certified that error appears in the above-identified patent and that said Letters Patent is hereby corrected as shown below:

Column 2, line 53, "the least two" should be --the at least two--.

Column 3, line 5, after "extension;" delete "and".

Column 5, line 10, "body 22" should be --body 20--.

Column 6, line 24, Delete "INVENTOR: Please verify.".

Column 6, line 28, "bend end" should be --bent end--.

Column 6, line 48, "enable" should be --enables--.

Column 7, line 25, "knee join" should be --knee joint--.

Column 7, line 61, "ligments" should be --ligaments--.

Column 10, line 1, after "wherein" insert --the--.

Signed and Sealed this
Twelfth Day of June, 2012

David J. Kappos
*Director of the United States Patent and Trademark Office*